United States Patent [19]

Hsu

[11] Patent Number: 5,369,128
[45] Date of Patent: Nov. 29, 1994

[54] METHOD OF SYNCHRONIZING FARROWING IN SWINE

[75] Inventor: Walter H. Hsu, Ames, Iowa

[73] Assignee: Iowa State University Research Foundation, Inc., Ames, Iowa

[21] Appl. No.: 80,350

[22] Filed: Jun. 21, 1993

[51] Int. Cl.$^5$ ................. A61K 31/557; A61K 31/415
[52] U.S. Cl. .................................... 514/573; 514/388; 514/396
[58] Field of Search ................. 514/388, 396, 530, 573

[56] References Cited

U.S. PATENT DOCUMENTS

| | | | |
|---|---|---|---|
| 3,202,660 | 8/1965 | Zeile et al. | 544/192 |
| 3,917,864 | 11/1975 | Karim | 514/530 |
| 4,089,951 | 5/1978 | Furr | 514/573 |
| 4,870,066 | 9/1989 | Edgerton et al. | 514/169 |

FOREIGN PATENT DOCUMENTS 422878  4/1991  European Pat. Off.

OTHER PUBLICATIONS

M. P. Boland et al., "Induction of Parturition in the Pig Using a New Prostaglandin Analogue (K11941)," *Theriogenology*, 17, 193–196 (1982).

D. P. Brooks et al., "The Water Diuretic Effect of the Alpha-2 Adrenoceptor Agonist, AGN 190851, Is Species-Dependent," *J. Pharmacol. Exp. Ther.*, 259, 1277–1282 (1991).

P. Chantaraprateep et al., "Investigation into the use of prostaglandin F$_2\alpha$(PGF$_2\alpha$) and oxytocin for the induction of farrowing," *Aust. Vet. J.*, 63, 254–256 (1986).

G. D. Dial et al., "Oxytocin precipitation of prostaglandin-induced farrowing in swine: Determination of the optimal dose of oxytocin and optimal interval between prostaglandin F$_2\alpha$ and oxytocin," *Am. J. Vet. Res.*, 48, 966–970 (1987).

J. R. Diehl, "Induction of Parturition in Swine with Prostaglandin F$_2$," *J. Anim. Sci.*, 38, 1229–1234 (1974).

S. Einarsson, "Comparative Trial with Natural Prostaglandin and an Analogue (Cloprostenol) in Inducing Parturition in Sows," *Acta Vet. Scand.*, 77, 321–326 (1981).

J. D. Fondacaro et al., "Antidiarrheal Activity of Alpha-2 Adrenoceptor Agonist SK&F 35886," *J. Pharmacol. Exp. Ther.*, 249, 221–228 (1989).

D. Hammond et al., "A farrowing management system using cloprostenol to control the time of parturition," *Vet. Rec.*, 106, 72–75 (1980).

I. Hermansson et al., "Use of a Prostaglandin Analogue (Cloprostenol) for Induction of Parturition in Pigs with Prolonged Gestation," *Nord. Vet. Med.*, 33, 349–353 (1981).

J. P. Hieble et al., "AGN 190851, A Potent, Peripherally Action, $\alpha_2$–Adrenoceptor Agonist," *Pharmacologist*, 33, 214 (1991).

W. H. Hsu, "Validation of an Innovative Approach to Synchronize Farrowing," Abstract of U.S. Dept. of Agriculture Grant No. 410-23-03, Identifying No. 0154327 (Federal Research in Progress) (1987).

T. Jen et al., "Amidines and Related Compounds. 6. Studies on Structure-Activity Relationships of Antihypertensive and Antisecretory Agents Related to Clonidine," *J. Med. Chem.*, 18, 90–99 (1975).

J. C. H. Ko et al., "Farrowing Induction with Cloprostenol-Xylazine Combination," *Theriogenology*, 31, 795–800 (1989).

J. C. H. Ko et al., "Xylazine Enhances Porcine Myometrial Contractility in Vitro: Possible Involvement of $\alpha_2$–Adrenoceptors and Ca$^{2+}$ Channels," *Biology of Reproduction*, 43, 614–618 (1990).

L. Kostov, "Biological and economic aspects of (List continued on next page.)

Primary Examiner—Marianne M. Cintins
Assistant Examiner—K. Weddington
Attorney, Agent, or Firm—Schwegman, Lundberg & Woessner

[57] ABSTRACT

The invention provides a method of synchronizing farrowing in swine comprising the steps of administering an effective amount of a prostaglandin and then administering to the sows an effective amount of a peripheral $\alpha_2$ adrenergic agonist, such that farrowing is induced.

20 Claims, No Drawings

OTHER PUBLICATIONS planned farrowing in large scale pig farming," *Proc. Int. Pig Vet. Soc.*, p. 4 (1980).

M. J. Martin et al., "Parturition Control in Sows with a Prostaglandin," *Theriogenology*, 24, 13–19 (1985).

J. W. McFarland et al., "Anticoccidial Activities of 7-Bromo-N-(2-Imidazolidinylidene)-1H-Indazol-6-Amine and Other $\alpha_2$ Adrenergic Agonists," *Antimicrob Agents Chemother.*, 36, 368–371 (1992).

J. A. Nathanson, "Phenyliminoimidazolidines, Characterization of a Class of Potent Agonists of Octopamine-Sensitive Adenylate Cyclase and Their Use in Understanding the Pharmacology of Octopamine Receptors," *Mol. Pharmacol.*, 28, 254–268 (1985).

R. R. Ruffolo et al., "Receptor Interactions of Imidazolines. XI. Alpha-Adreneregic and Antihypertensive Effects of Clonidine and Its Methylene-Bridged Analog, St 1913", *Pharmacology*, 25, 187–201 (1982).

R. R. Ruffolo et al., "Interaction of Clonidine, Its Methylene-Bridged Analog, St 1913, and the Benzylic Hydroxyl-Substituted Derivative, St 1965, with $\alpha_1$-and $\alpha_2$-Adrenoreceptors," *J. Auton. Pharmac.*, 3, 185–193 (1983).

D. D. Smyth et al., "Opposite Rank Order of Potency for Alpha-2 Adrenoceptor Agonists on Water and Solute Excretion in the Rat: Two Sites and/or Receptors?," *J. Pharmacol. Exp. Ther.*, 261, 1080–1086 (1992).

H. L. Winship et al., "Effects of Attending Farrowing," *University of Illinois at Urbana–Champaign Swine Research Reports*, 1–2 (Dec. 1982).

F. Cerne et al., "Clinical evaluations of a new prostaglandin analog in pigs: I. Control of parturition and of the MMA-syndrome" *Theriogenology*, 16, 459–457 (1981).

METHOD OF SYNCHRONIZING FARROWING IN SWINE

GOVERNMENT SUPPORT

The present invention was made with government support under Section 1433 Formula Funds for Animal Health, Accession No. C154327, awarded by the United States Department of Agriculture. The Government has certain rights in this invention.

FIELD OF THE INVENTION

This invention relates generally to methods of initiating farrowing in swine. More specifically, the invention relates to the use of peripheral $\alpha_2$ adrenergic agonists to synchronize farrowing in swine.

BACKGROUND OF THE INVENTION

A pork producer's profit depends on the cost of feed and the market price for pork, and on the ability to attain a high percentage of live births and pigs weaned per litter. Furthermore, a pork producer's profit is contingent on controlling the cost of personnel used to assist in the farrowing operation. Thus, any significant technological advance useful in optimizing efficiency and reducing personnel costs may receive wide acceptance among pork producers.

Having experienced and skilled personnel available to assist during farrowing and the neonatal period is important for several reasons. When giving birth to large litters a sow will often tire. This results in the stillbirth of the last few pigs of the litter who are unable to escape the uterus and reach air before suffocating. Further, pigs are born without hair and, as such, are susceptible to temperature changes. Hypothermia can often cause the death of young pigs.

It should also be appreciated that the litter may be larger than the number of functional nipples available on the sow. Nipples on the upper chest are also typically more productive than those at the sow's hindquarter. Thus, small pigs that cannot compete with their litter mates may be pushed to the less productive nipples and not receive the nutrients needed to grow or even survive. Specifically, since pigs receive their immunity to disease through the milk of the sow, undernourished pigs are very susceptible to diseases and infections. Further, weakened pigs may be slowed and unable to move quickly enough to avoid being accidentally crushed by the sow in the pen.

With proper care, the rate of pig survival can be greatly increased. The assisting personnel can help the sow as she farrows thereby helping her when she tires and reducing the number of stillborns. Obstructions such as mucous may be cleaned from the nostrils of newborn pigs to reduce stress and/or even prevent suffocation. Since sows are receptive to pigs born of another sow, cross-fostering of pigs can be practiced. By proportioning the number of pigs per sow and placing pigs of approximately the same size with the same sow, better overall nutrition of all the newborn pigs is assured.

Maintaining a high birth rate in a herd of swine and using personnel efficiently so as to minimize costs has lead pork producers to seek methods for synchronizing farrowing. In the past, pork producers have sought to synchronize farrowing among the sows of a herd so as to reduce the man-hours required to provide care and increase newborn pig survival.

Synchronized weanings have been used in an effort to synchronize subsequent farrowings. Specifically, after the sows have all been nursing present litters for about three weeks, the litters are weaned. Four to six days after weaning, the sows are again ready for breeding. By breeding all the sows on or about the same day, farrowings can be synchronized to fall within a relatively short period. While this technique is more efficient than random breeding, biological variations in the sows of the herd may result in farrowing taking place over as much as a seven day period. Also, farrowing can occur at any time of the day or night.

Another means of synchronizing farrowing in swine herds has been via the use of various veterinary pharmaceuticals. However, the extreme potency of some of the drugs employed for uterine stimulation can cause injury to the sows uterus during delivery. Steroids such as progesterone or "progestin" may be administered to sows late in the gestation period so as to extend gestation and delay farrowing. However, the utilization of progesterone to delay farrowing has been shown to increase the rate of stillbirths and incidents of dystocia or abnormal labor.

Prostaglandin F$_{2\alpha}$ (PGF$_{2\alpha}$), or its analogs, e.g., cloprostenol, may also be administered to sows so as to induce parturition or farrowing. The use of prostaglandins to synchronize farrowing in a herd is, however, of limited effectiveness. The average time for responding to PGF$_{2\alpha}$ or cloprostenol treatment is 33 hours, with a range of 15–48 hours (L. Hermansson et at., *Nord. Vet. Med.*, 33, 349–353 (1981)). This response variation is too great to allow for the potential benefits of farrowing induction.

Recently, oxytocin was used in combination with PGF$_{2\alpha}$ or its analog to facilitate induction of farrowing (P. Chantaraprateep et at., *Aust. Vet. J.*, 63, 254–256 (1986); and G. D. Dial et al., *Am. J. Vet. Res.*, 48, 966–970 (1987)). However, this approach is not satisfactory because the procedure is not practical. It results in highly variable onset of the induced farrowing or potential loss of piglets resulting from dystocia induced by these drugs.

The combination of PGF$_{2\alpha}$ and xylazine to induce farrowing has also been studied (J. C. H. Ko et al., *Theriogenology*, 31, 795–800 (1989)). This study clearly indicates that this combination could be used to reliably and effectively synchronize farrowing. Xylazine is an $\alpha_2$-adrenergic agonist, and $\alpha_2$-agonists are potent myometrial contractants in pigs. These drugs offer an alternative to oxytocin for the stimulation of myometrial contraction. In addition, their effects on the myometrium can be reversed by $\alpha_2$-adrenergic antagonists, unlike the effects oxytocin. However, xylazine's sedative effect may not be desirable when used as an oxytocic agent. Thus, a need exists for a safe and effective method for synchronizing farrowing in pregnant sows, particularly without sedative effects.

SUMMARY OF THE INVENTION

In accordance with the invention, there is provided a method of initiating farrowing in a pregnant sow, particularly synchronizing farrowing in pregnant sows in a herd to a single, condensed target period. This method involves administering an amount of a prostaglandin effective to stimulate luteolysis and remove the corpus luteum, and administering an amount of a peripheral $\alpha_2$ adrenergic agonist effective to increase uterine contractions and induce parturition. For best results, preferably the sows can be bred using synchronized weaning techniques.

Preferably, the invention is directed to a method of synchronizing farrowing in pregnant sows, through the use of prostaglandin $F_{2\alpha}$ followed by a peripheral $\alpha_2$ adrenergic agonist to initiate farrowing. By synchronizing farrowing throughout the herd, the producer is allowed to devote substantial resources to the birth of offspring at that time. Otherwise, the birth of offspring may occur randomly creating a continual demand for time from the producer as well as other skilled labor.

DETAILED DESCRIPTION

The invention is a method of synchronizing farrowing in pregnant sows in a herd by administering a prostaglandin to each pregnant sow and, after a preselected period of time, administering a peripheral $\alpha_2$ adrenergic agonist to each pregnant sow. This method induces farrowing with a high degree of synchrony by terminating progesterone production by the corpora lutea, expanding the birth canal, and producing uterine contractions. The degree of synchrony achieved by use of the present invention is preferably about 2-4 hours. That is, using the method of the present invention the pregnant sows in a herd preferably birth within about 2-4 hours of each other.

Prostaglandins

The first step of the invention is the administration of a prostaglandin to the pregnant sows of a herd. As used herein, the term "prostaglandin" refers to any prostaglandin or prostaglandin analog, which is either naturally occurring or synthetically produced, and which has the characteristics of initiating farrowing, specifically luteolysis, in a pregnant sow. Compositions comprising naturally occurring prostaglandin $F_{2\alpha}$ include those available under the trademark Lutalyse® from Upjohn Company. Also useful are analogues of prostaglandin $F_{2\alpha}$, such as: fenprostalene (($\pm$)-9$\alpha$,11$\alpha$,15$\alpha$-trihydroxy-16-phenoxy-17,18,19,20-tetranorprosta-4,5,13-trans-trienoic acid methyl ester), a synthetic analog of prostaglandin $F_{2\alpha}$ available from Syntex Inc.; cloprostenol (7-[2-[4-(3-chlorophenoxy)-3-hydroxy-1-butenyl]-3,5-dihydroxycyclopently]-5-heptenoic acid), an aryloxymethyl analog of prostaglandin $F_{2\alpha}$ available from Imperial Chemical Industries; fluprostenol (9,11,15-trihydroxy-15-methylprosta-4,5,13-trien-1-oic acid methyl ester) available from Haver/Diamond Scientific; prostalene (7-[3-hydroxy-2-(3-hydroxy-1-octenyl)-5-oxocyclopentyl]-5-heptenoic acid) available from Syntex; alfaprostol ([1R-[1$\alpha$(Z), 2$\beta$(S*), 3$\beta$,5$\alpha$]]-7-[2-(5-cyclohexyl-3-hydroxy-1-pentynyl)-3,5-dihydroxycyclopentyl]-5-heptenoic acid methyl ester) available from Hoffman La Rouche; and the pharmaceutically acceptable salts of prostaglandin, e.g., the tromethamine salt of prostaglandin $F_{2\alpha}$ (dinoprost tromethamine), and its analogs. The pharmaceutically acceptable salts thereof include, but are not limited to, the addition salts of inorganic and organic acids, which are commercially available, such as the tromethamine and sodium salts.

Preferably, the prostaglandin is administered through any number of formats known to those of skill in the art. Dosages generally range from about 0.01 mg to about 10 mg depending on the body weight. Preferably, the prostaglandin is administered to a pregnant sow in an amount of about 0.1 µg to about 10 µg per kilogram of body weight. The prostaglandin is preferably administered about 25-50 hours before the beginning of the target period. The target period begins preferably about 48-72 hours prior to the end of the gestation period for swine. Typically, the gestation period is about 112-116 days, preferably about 113-115 days.

Peripheral $\alpha_2$ Adrenergic Agonists

Peripheral $\alpha_2$ adrenergic agonists, i.e., peripheral $\alpha_2$ adrenoreceptor agonists, activate $\alpha_2$ adrenergic receptors outside the central nervous system. These compounds in general inhibit norepinephrine release from the sympathetic nerve terminal, inhibit acetylcholine release from the parasympathetic nerve terminal, inhibit insulin release from the B-cells of the pancreatic islets, inhibit gastrointestinal contractibility, increase vascular and uterine smooth muscles to enhance vasoconstriction and uterine contractibility.

Preferred peripheral $\alpha_2$ adrenergic agonists for use in the present invention include: 2-[(2,6-dichlorophenyl)-methyl-1H-imidazole, available under the designation "ST-1913"; 5-bromo-N-(4,5-dihydro-1H-imidazol-2-yl-amino)-1,2,3,4-tetrahydro-6-quinoxalinamine, available under the designation "AGN 190851"; and N-(2,6-dimethylphenyl)-4,5-dihydro-1H-imidazol-2-amine, available under the designation "SKF 35886". As used herein, the term "peripheral $\alpha_2$ adrenergic agonists" is not limited to these three discrete chemical moieties and their salts, but includes the derivatives and analogs thereof, which are recognized to function as peripheral $\alpha_2$ adrenergic agonists. A number of such derivatives have been disclosed in the patent and scientific literature. The useful pharmaceutically acceptable salts thereof include, but are not limited to, the addition salts of inorganic and organic acids, such as the hydrochloride, bitartrate, and phosphate salts.

The use of a single peripheral $\alpha_2$ adrenergic agonist is preferred to minimize side effects and to simplify administration, for example. However, the administration of a plurality, e.g., 2-5, of such agents is within the scope of the present invention, and may be useful to increase contractions and induce parturition in certain sows.

The peripheral $\alpha_2$ adrenergic agonists, administered singly or in combination, are preferably administered in an amount effective to induce farrowing in about 1-3 hours. Preferably, the peripheral $\alpha_2$ adrenergic agonist is administered in an amount of about 0.01-1.0 mg/kg body weight of the animal. As stated previously, the peripheral $\alpha_2$ adrenergic agonist is administered subsequent to the administration of the prostaglandin. Preferably, the peripheral $\alpha_2$ adrenergic agonist is administered about 18-24 hours after the administration of the prostaglandin. Administration can be by various parenteral routes of administration of the agents, such as subcutaneous, intramuscular, or intravenous administration, in combination with a suitable liquid vehicle. Preferably, administration is intramuscularly.

ST-1913

2-[(2,6-Dichlorophenyl)methyl]-4,5-dihydro-1H-imidazole, available under the designation "ST-1913" from Boehringer Ingelheim G.m.b.H., has the formula:

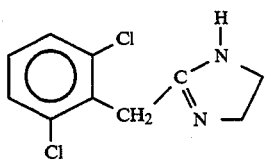

Its preparation, properties, and salts, e.g., hydrochloride salt, are extensively discussed in the scientific literature. See, for example, J. W. McFarland et al., *Antimicrob Agents Chemother.*, 36, 368 (1992); J. A. Nathanson, *Mol. Pharmacol.*, 28, 254 (1985); R. R. Ruffolo et al., *J. Auton. Pharmacol.*, 3, 185 (1983); T. Jen et al., *J. Med. Chem.*, 18, 90 (1975); and R. R. Ruffolo et al., *Pharmacology*, 25, 187 (1982).

AGN 190851

5-Bromo-N-(4,5-dihydro-1H-imidazol-2-yl-amino)-1,2,3,4-tetrahydro-6-quinoxalinamine, available under the designation "AGN 190851" from Allargan Inc., Irvine, Calif., has the formula:

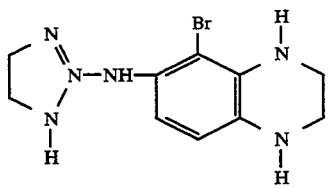

Its preparation, properties, and salts, e.g., hydrochloride salt, are discussed in European Patent Application EP 422878 (published Apr. 17, 1991); J. P. Hieble et al., *Pharmacologist*, 33, 214 (1991); and D. P. Brooks et al., *J. Pharmacol. Exp. Ther.*, 259, 1277 (1991), for example.

SKF 35886

N-(2,6-dimethylphenyl)-4,5-dihydro-1H-imidazol-2-amine, available under the designation "SKF 35886" from SmithKline Beecham Pharmaceuticals, has the formula:

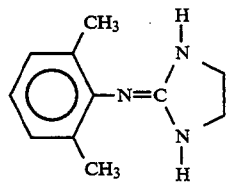

Its preparation, properties, and salts, e.g., hydrochloride salt, are discussed in the scientific literature. See, for example, J. D. Fondacaro et at., *J. Pharmacol. Exp. Ther.*, 249, 221 (1989); and D. D. Smyth et al., *J. Pharmacol. Exp. Ther.*, 261, 1080 (1992).

The following examples illustrate the method of the invention including the application of peripheral $\alpha_2$ adrenergic agonists within an environment of use. These working examples should be viewed simply and purely as illustrative and not as limiting of the present invention.

EXAMPLE 1

In vitro experiments were conducted on uterine strips from diestrous sows to study the contractile effect of ST-1913 on myometrium. Water-jacketed tissue baths maintained at 38° C., containing 10 ml of Tyrode's solution (137 mM NaCl, 4 mM KCl, 1 mM $CaCl_2$, 0.4 $MgCl_2$, 11 mM dextrose, and 12 mM $NaHCO_3$) and perfused with 95% $O_2$, 5% $CO_2$, were used to hold 2 cm $\times$ 0.3 cm uterine strips. The tissues were attached via cotton thread to force displacement transducers (FT03C, Grass Instrument Co., Quincy, Mass.) and adjusted to a 2 gram tension. Development of isometric tension was monitored with a multiple-channel recorder (R411, Beckman Instruments Inc., Schiller Park, Ill.).

All strips were initially exposed to $1 \times 10^{-5}M$ carbachol to determine viability. This concentration caused maximal contractile. Strips were washed and were allowed to equilibrate for over 10 minutes before the baseline tension was readjusted to 2 grams. The ST-1913 (hydrochloride salt dissolved in water) treatment was made at 10 minute intervals by adding it directly into tissue baths in cumulative doses using the 0.1 ml volume.

In an experiment with uterine strips obtained from a 110 day pregnant sow, ST-1913 ($10^{-8}$–$10^{-5}M$) caused a dose-dependent increase in myometrial contractility. An $\alpha_2$-adrenergic antagonist yohimbine ($3 \times 10^{-8}$, $10^{-7}$, and $3 \times 10^{-7}M$) caused a dose-dependent inhibition of myometrial contractions induced by ST-1913. In contrast an $\alpha_1$-adrenergic antagonist prazosin ($10^{-6}M$) failed to antagonize this effect of ST-1913. These results suggest: (1) ST-1913-induced myometrial contactility is mediated by $\alpha_2$-adrenergic receptors; and (2) ST-1913 offers potential for synchronization of farrowing without having significant CNS depressant activities like xylazine.

EXAMPLE 2

Six crossbred, multiparous sows, weighing between 182 and 238 kg were randomly assigned to the following two groups of three sows each: 1) cloprostenol and 2) cloprostenol+AGN 190851. Cloprostenol (250 µg/sow) was administered intramuscularly (i.m.) to four sows on the 112th day of pregnancy, and to two sows on the 111th day of pregnancy at 11:30 a.m. AGN 190851 (0.2 mg/kg) or 0.9% NaCl was administered i.m. 20 hours after the cloprostenol treatment.

All sows were observed continuously after the second treatment from 7:30 a.m. until the end of the experiment when the placental membrane was expelled. After the start of farrowing, if the interval between successive piglets in a litter was greater than 30 minutes, sows were examined for dystocia. Manual assistance was used only when necessary.

The following parameters were examined and averaged in each group: farrowing interval (interval from second treatment to the first pig born); farrowing time (interval from first piglet born to the end of placental expulsion); number of pigs born per sow in each group; number of pigs born alive per sow in each group. Student's t-test was used to test for differences between means of end points.

Sows treated with cloprostenol-AGN 190851 had a significantly (P<0.05) shorter mean farrowing interval than the ones treated with cloprostenol alone (Tables 1 & 2). No significant differences were observed between the two treatment groups with regards to the farrowing time, number of pigs born per sow, and number of pigs born alive per sow. None of the sows receiving AGN 190851 were sedated.

As this example shows treatment with a peripheral $\alpha_2$ adrenergic agonist would allow a more precise control of farrowing that can occur during normal working hours to allow for increased attendance by caretakers.

TABLE 1

Farrowing Induction with Cloprostenol-AGN 190851 Combination

| Animal # | 1 | 2 | 3 | 4 | 5 | 6 |
|---|---|---|---|---|---|---|
| BW (kg) | 238 | 182 | 193 | 193 | 195 | 185 |
| Day of pregnancy when cloprostenol was given | 112 | 112 | 111 | 111 | 112 | 112 |
| Cloprostenol | yes | yes | yes | yes | yes | yes |
| AGN 190851 | no | yes | no | yes | yes | no |
| Farrowing time (min) | 300 | 40 | 185 | 52 | 30 | 225 |
| Farrowing interval (min) | 315 | 155 | 180 | 245 | 205 | 235 |
| # pigs born | 10 | 12 | 12 | 13 | 14 | 13 |
| # pigs born alive | 10 | 12 | 12 | 11 | 14 | 13 |

TABLE 2

Effect of Treatment on Farrowing Induction

| Treatment | Farrowing time | Farrowing interval | Still birth (%) |
|---|---|---|---|
| CS: | 237 ± 58 | 243 ± 68 | 0 |
| CA: | 41 ± 11* | 202 ± 45 | 5 ± 9 |

AH values are shown as mean ± SD (n=3).
*P < 0.05 compared to CS.
CS: Cloprostenol-safine.
CA: Cloprostenol-AGN 190851.

All patents and publications cited hereinabove are incorporated by reference herein. The foregoing specification, examples, and data provide a basis for understanding the invention. The invention can be made in a variety of embodiments without departing from the spirit and scope of the invention. Accordingly, the invention resides in the claims hereinafter appended.

What is claimed is:

1. A method of synchronizing farrowing in pregnant sows in a herd; said method comprising:
   (a) administering an effective amount of a prostaglandin to each pregnant sow; and
   (b) subsequently administering an effective amount of a peripheral $\alpha_2$ adrenergic agonist to each pregnant sow.

2. The method of claim 1 wherein said prostaglandin is selected from the group consisting of dinoprost tromethamine, cloprostenol, fluprostenol, prostalene, fenprostalene, alfaprostol, or mixtures thereof.

3. The method of claim 1 wherein said peripheral $\alpha_2$ adrenergic agonist comprises 2-[(2,6-dichlorophenyl)-methyl]-4,5-dihydro-1H-imidazole).

4. The method of claim 1 wherein said peripheral $\alpha_2$ adrenergic agonist comprises 5-bromo-N-(4,5-dihydro-1H-imidazol-2-yl-amino)-1,2,3,4-tetrahydro-6-quinoxalinamine.

5. The method of claim 1 wherein said peripheral $\alpha_2$ adrenergic agonist comprises N-(2,6-dimethylphenyl)-4,5-dihydro-1H-imidazol-2-amine.

6. The method of claim 1 wherein said peripheral $\alpha_2$ adrenergic agonist is administered in an amount of about 0.01–1.0 mg/kg body weight.

7. The method of claim 2 wherein said prostaglandin is administered in an amount of about 0.1–10 µg/kg body weight.

8. The method of claim 7 wherein said prostaglandin is administered about 18–24 hours prior to administration of the peripheral $\alpha_2$ adrenergic agonist.

9. A method of synchronizing farrowing in pregnant sows; said method comprising:
   (a) administering an effective amount of prostaglandin $F_{2\alpha}$ to each pregnant sow; and
   (b) subsequently administering an effective amount of a peripheral $\alpha_2$ adrenergic agonist to each pregnant sow.

10. The method of claim 9 wherein said prostaglandin $F_{2\alpha}$ is administered in the form of a pharmaceutically acceptable salt.

11. The method of claim 9 wherein said peripheral $\alpha_2$ adrenergic agonist comprises 2-[(2,6-dichlorophenyl)-methyl]-4,5-dihydro-1H-imidazole).

12. The method of claim 9 wherein said peripheral $\alpha_2$ adrenergic agonist comprises 5-bromo-N-(4,5-dihydro-1H-imidazol-2-yl-amino)-1,2,3,4-tetrahydro-6-quinoxalinamine.

13. The method of claim 9 wherein said peripheral $\alpha_2$ adrenergic agonist comprises N-(2,6-dimethylphenyl)-4,5-dihydro-1H-imidazol-2-amine.

14. The method of claim 9 wherein said peripheral $\alpha_2$ adrenergic agonist is administered in an amount of about 0.01–1.0 mg/kg body weight.

15. The method of claim 9 wherein said prostaglandin $F_{2\alpha}$ is administered in an amount of about 0.1–10 µg/kg body weight.

16. The method of claim 9 wherein said prostaglandin $F_{2\alpha}$ is administered about 18–24 hours prior to administration of the peripheral $\alpha_2$ adrenergic agonist.

17. A method of initiating farrowing in a pregnant sow, said method comprising the steps of:
   (a) administering an amount of a prostaglandin effective to stimulate luteolysis; said prostaglandin selected from the group consisting of dinoprost tromethamine, cloprostenol, fluprostenol, prostalene, fenprostalene, alfaprostol, or mixtures thereof; and
   (b) subsequently administering an amount of a peripheral $\alpha_2$ adrenergic agonist effective to increase uterine contractions, said peripheral $\alpha_2$ adrenergic agonist selected from a group consisting of 2-[(2,6-dichlorophenyl)methyl]-4,5-dihydro-1H-imidazole), 5-bromo-N-(4,5-dihydro-1H-imidazol-2-yl-amino)-1,2,3,4-tetrahydro-6-quinoxalinamine, and N-(2,6-dimethylphenyl)-4,5-dihydro-1H-imidazol-2-amine.

18. The method of claim 17 wherein said prostaglandin $F_{2\alpha}$ is administered in an amount of about 0.1–10 µg/kg body weight.

19. The method of claim 17 wherein said prostaglandin is administered about 18–24 hours prior to administration of the peripheral $\alpha_2$ adrenergic agonist.

20. The method of claim 17 wherein said peripheral $\alpha_2$ adrenergic agonist is administered in an amount of about 0.01–1.0 mg/kg body weight.

* * * * *